United States Patent [19]

Scarano et al.

[11] Patent Number: 5,099,001
[45] Date of Patent: Mar. 24, 1992

[54] PROCESS FOR THE PRODUCTION OF THYROGLOBULIN

[75] Inventors: Louis Scarano; H. Glenn Corkins, both of Harriman, N.Y.

[73] Assignee: Nepera, Inc., Harriman, N.Y.

[21] Appl. No.: 456,682

[22] Filed: Dec. 28, 1989

[51] Int. Cl.$^5$ .............................. A61K 35/14
[52] U.S. Cl. ................... 530/380; 530/395; 530/397
[58] Field of Search .............. 530/380, 395, 397

[56] References Cited

U.S. PATENT DOCUMENTS 3,970,746  7/1976  Premachandra .................. 436/541
4,851,509  7/1989  Jolles et al. ........................ 530/330

OTHER PUBLICATIONS

Angem. Chem. Int. Ed. Engl., 20, pp. 305-325, Gros et al., 1981, "Polymeric Antitumor Agents on a Molecular and on a Cellular Level?".

Primary Examiner—C. Warren Ivy
Assistant Examiner—Raymond Covington
Attorney, Agent, or Firm—Millen, White & Zelano

[57] ABSTRACT

The invention relates to a process for the production of thyroglobulin, which is used in the treatment of hypothyroidism, from hog thyroid glands. Ground hog thyroid glands are subjected to saline digestion to produce a thyroglobulin extract. The extract is precipitated by pH adjustment and then heated to a denaturing temperature. The denatured precipitated thyroglobulin solution is subjected to a separation step to produce crude wet thyroglobulin solids. The crude thyroglobulin solids are defatted and dewatered by solvent extraction. The resultant defatted thyroglobulin product can then be further worked up, for example, by drying, milling, and screening, to produce a powdered product. In order to achieve a final product having a $T_4/T_3$ ratio of 2.6–3.4 and upon proteolysis a minimum of 0.7 μg/mg of levothyronine and 2.1 μg/mg of liothyronine, the time periods for the precipitating, denaturing, and/or defatting steps are carefully controlled so that the $T_4/T_3$ ratio is within this desired range.

18 Claims, 1 Drawing Sheet

PROCESS FOR THE PRODUCTION OF THYROGLOBULIN

BACKGROUND OF THE INVENTION

This invention relates to processes for the production of thyroglobulin. Thyroglobulin, a glycoprotein produced by the thyroid gland, functions as a source of the active hormones levothyroxine ($C_{15}H_{11}I_4NO_4$, also referred to as thyroxine) and triiodothyronine ($C_{15}H_{12}I_3NO_4$, also known as liothyronine and thyronine). These hormones are formed from the iodinated tryosine moieties of thyroglobulin and are released into blood by proteolysis of thyroglobulin.

Thyroglobulin is utilized in the treatment of hypothyroidism, e.g., as an orally administered thyroid supplement. Specific diseases which can be treated with thyroglobulin include cretinism, myxedema, and ordinary, primary, secondary, and/or tertiary hypothyroidism. The components, structure, physical properties, and biological activity of thyroglobulin are known in the art. The product is available is prescription form. See, for example, Physicians Desk Reference 1989, p. 1593, "Proloid" ® brand of thyroglobulin; S. Lissitzky, Pharmacol. Ther. B 2, 219 (1976); and G. Levy et al., Am. J. Pharm. 133, 255 (1961).

The source of commercially produced thyroglobulin is the thyroid glands of hogs. These glands are ground and digested in a saline solution. After separating the meat tissue, the resulting aqueous solution is further treated (e.g., precipitation, denaturing, defatting, and drying).

The thyroglobulin product obtained is a free-flowing powder of cream to tan color and having a slight, characteristic odor. Powdered thyroglobulin is used, for example, in the production of Proloid ® tablets.

As mentioned above, thyroglobulin functions as a source of thyroxine and triiodothyronine. Thus, an important parameter associated with thyroglobulin is the ratio of thyroxine, i.e., $T_4$, to triiodothyronine, i.e., $T_3$, also known as the $T_4/T_3$ ratio, as well as the absolute amounts of these active ingredients upon proteolysis.

The United States Pharmacopea (USP) has recently changed the USP specification for thyroglobulin and thyroglobulin tablets in order to provide the physician with a standard dosage range based on active $T_4$ and $T_3$ levels, since both synthetic and glandular products are now available to physicians. This new specification insures better dosimetry with the glandular-derived product, particularly when compared to the competitive and well-defined synthetic thyroid products.

The older USP XX specification for thyroglobulin required a minimum of 0.7% of organically bound iodine as determined by the potassium carbonate fusion technique (see USP XX, pp. 799-800). This specification and classical preparations, as well as that for the formulated tablets (p. 800), allowed for significant fluctuation of active ingredient (as available $T_4$ and $T_3$ constituents) when compared to synthetic thyroid preparations of known absolute active ingredient composition [see S. Ingbar et al., New Eng. J. Med. 270, 439 (1964)]. The most recent USP XXII specification on formulated product (p. 1372) specifies the ratio of $T_4/T_3$ of 3 and requires that the tablets contain 85-115% of the labeled amount of levothyroxine and 90-110% of the labeled amount of liothyronine, which labeled amounts are equal to 36 µg levothyroxine and 12 µg of liothyronine for each 65 mg of the labeled content of glandular derived thyroglobulin.

At the same time, the specification for the glandular derived product was simply set at 90-110% of the labeled amounts of levothyroxine and liothyronine. These newer specifications require the production of glandular derived thyroglobulin with allowable $T_4/T_3$ ratios of 2:4-3.6 and absolute levels not less than 0.7 µg/mg of liothyronine and 2.1 µg/mg levothyroxine as determined by the proteolytic enzyme/HPLC assay.

Although conventional processes for the production of thyroglobulin routinely met USP XX specifications, the new USP XXII specification could not consistently be met with existing processes since the old process routinely product with $T_4/T_3$ ratios which could not be used to produce certain of the available dosage forms under the newer specification for dosage forms.

In prior in-house processes, the desired $T_4/T_3$ ratio and absolute values of levothyroxine and liothyronine of product thyroglobulin which could subsequently be employed to prepare dosage forms meeting USP XXII specifications were only achieved in about 30% of the process runs. Thus, such processes were economically disadvantageous.

SUMMARY OF THE INVENTION

The present invention provides a process for the production of thyroglobulin having a $T_4/T_3$ ratio of about 2.6-3.4 and absolute levels of not less than about 0.65-0.75, especially not less than 0.7 µg/mg of liothyronine and not less than about 2.0-2.2, especially not less than 2.1 µg/mg of levothyroxine.

The process according to the invention consistently meets the desired $T_4/T_3$ ratio and levothyroxine/liothyronine absolute values in, e.g., 60%, 80%, and 100% of the runs.

The invention thus relates to a process for the production of thyroglobulin comprising saline digestion of hog thyroid glands, precipitation of thyroglobulin by pH adjustment, denaturation of thyroglobulin by subjecting it to heat, and defatting/dewatering thyroglobulin by alcohol extraction under reflux, the improvement comprising: performing the precipitating, denaturing, and defatting/dewatering steps for times sufficient to achieve a thyroxine-to-triiodothyronine ratio ($T_4/T_3$ ratio) of about 2.6-3.4 and absolute concentrations of thyroxine and triiodothyronine on proteolysis.

The invention further relates to:

a process for the production of thyroglobulin having a thyroxine-to-triiodothyronine ratio ($T_4/T_3$ ratio) comprising saline digestion of mammalian thyroid glands to release thyroglobulin, precipitation of thyroglobulin by pH adjustment, denaturation of thyroglobulin by heating, and defatting thyroglobulin by extraction with alcohol, the improvement comprising:

correlating the precipitating, denaturing, and defatting steps whereby the duration of the precipitating step is selected to produce thyroglobulin having a first $T_4/T_3$ ratio substantially greater than 2.6 and the durations of the denaturing and defatting steps are selected in correlation with said precipitating step duration to lower said $T_4/T_3$ value greater than 2.6 to a final value in the range of 2.6-3.4 and absolute levels of not less than 0.7 µg/mg liothyronine and not less than 2.1 µg/mg levothyroxine.

In another aspect, the invention provides:

a process for the production of thyroglobulin from thyroglobulin extract produced from the saline digestion of hog thyroid glands, comprising:

(a) precipitating thyroglobulin by pH adjustment of the thyroglobulin extract, (b) denaturing the thyroglobulin extract by heating, (c) defatting thyroglobulin by extraction with alcohol under reflux, and (d) isolation and drying of final product wherein the denaturing and defatting steps are performed for a time sufficient to achieve a thyroxine-to-triiodothyronine ($T_4/T_3$) ratio in the defatted thyroglobulin of about 2.6–3.4 and the stated values of levothyroxine and liothyronine.

The invention further relates to: a process for the production of thyroglobulin having a thyroxine-to-triiodothyronine ($T_4/T_3$) ratio of about 2.6–3.4 from a mammalian thyroglobulin extract, comprising:

(a) precipitating the thyroglobulin extract by adjusting pH and by heating for a time sufficient to provide a $T_4/T_3$ ratio substantially greater than 2.6;

(b) determining by parametric experiments the time of subsequent denaturing and defatting treatments of the resultant thyroglobulin effective to denature and defat the thyroglobulin and to lower the $T_4/T_3$ ratio greater than 2.6 to a value in the range of 2.6–3.4 and absolute levels of not less than 0.7 µg/mg, liothyronine and not less than 2.1 µg/mg levothyroxine.

(c) denaturing thyroglobulin by heating to a temperature higher than the temperature of precipitation and maintaining the higher temperature in accordance with the time determined in step (b); and (d) defatting thyroglobulin by extraction with alcohol under reflux in accordance with the time determined in step (b).

The invention also relates to:

a process for the production of thyroglobulin from thyroglobulin extract produced from the saline digestion of hog thyroid glands, comprising:

(a) precipitating thyroglobulin by pH adjustment of said thyroglobulin extract;

(b) denaturing said thyroglobulin extract by heating; and (c) defatting thyroglobulin by extraction with alcohol; wherein the durations of steps (b) and (c) are selected to adjust for an increase in $T_4/T_3$ ratio occurring during step (a) and wherein when the process is repeated at least 60% of the process runs yield defatted thyroglobulin product with a $T_4/T_3$ ratio of about 2.6–3.4 and absolute values of not less than 0.7 µg/mg liothyronine and not less than 2.1 µg/mg levothyroxine.

Another aspect of the invention is:

a process for the production of thyroglobulin from thyroglobulin extract produced from the saline digestion of hog thyroid glands, comprising:

(a) precipitating thyroglobulin by pH adjustment of the thyroglobulin extract;

(b) denaturing the thyroglobulin extract by heating; and (c) defatting thyroglobulin by extraction with alcohol;

wherein the duration of steps (b) and (c) are sufficient to decrease the $T_4/T_3$ ratio of the thyroglobulin and wherein when the process is repeated at least 60% of the process runs yield a defatted thyroglobulin product with a $T_4/T_3$ ratio of about 2.6–3.4 and absolute levels of not less than 0.7 µg/mg liothyronine and not less than 2.1 µg/mg liothyroxine.

In another embodiment, the invention provides:

a process for the production of thyroglobulin from crude thyroglobulin obtained from denatured thyroglobulin extract, comprising:

defatting thyroglobulin by extraction with alcohol under reflux, wherein the defatting step is performed for a time sufficient to achieve a thyroxine-to-triiodothyronine ($T_4/T_3$) ratio in the defatted thyroglobulin of about 2.6–3.4.

A further aspect of the invention is: a process for the production of thyroglobulin having a thyroxine-to-triiodothyronine ($T_4/T_3$) ratio of about 2.6–3.4 from denatured mammalian thyroglobulin obtained having a $T_4/T_3$ ratio substantially greater than 2.6, comprising:

defatting thyroglobulin by extraction with alcohol for a time sufficient to achieve a $T_4/T_3$ ratio in the defatted thyroglobulin of about 2.6–3.4 and absolute levels of not less than 0.7 µg/mg liothyronine and not less than 2.1 µg/mg levothyroxine, the time having been determined by parametric experiments varying defatting time for a given $T_4/T_3$ ratio in said denatured mammalian thyroglobulin.

The invention also provides:

a process for the production of thyroglobulin comprising saline digestion of hog thyroid glands, precipitating thyroglobulin by pH adjustment, denaturing thyroglobulin by heating, and defatting thyroglobulin by extraction with alcohol under reflux, wherein the improvement comprises:

performing the precipitating, denaturing, and defatting steps for a time sufficient to achieve a thyroxine-to-triiodothyronine ratio ($T_4/T_3$ ratio) of about 2.6–3.4.

In a preferred embodiment, the invention provides:

a process for the production of thyroglobulin comprising:

(a) digesting hog thyroid glands by adding ground hog thyroid glands to an aqueous saline solution of NaCl and sodium salicylate at a temperature of about 0°–5° C. and for a time period of about 16–24 hours;

(b) following digestion, separating the resultant mixture into waste tissue and an aqueous solution of thyroglobulin extract;

(c) heating the extract to about 46° C., adjusting the pH thereof to about 4.4, and then heating the extract to about 86° C., wherein the total time required for the performance of stage (c) is about 0.5 hours;

(d) denaturing and precipitating the extract by holding the filtrate at a temperature of about 86° C. for a time period of about 3 hours;

(e) cooling the extract to a temperature of about 60° C. and, while cooling, filtering the extract to obtain a filter cake of wet crude thyroglobulin;

(f) forming a slurry of the wet crude thyroglobulin with alcohol and heating the resultant slurry to reflux, thereby defatting the wet thyroglobulin by extraction, wherein extraction is performed for a time period of about 1.5 hours;

(g) filtering the slurry following extraction to again obtain a filter cake of once-extracted thyroglobulin;

(h) forming a slurry by mixing once-extracted thyroglobulin with alcohol and again performing extraction in accordance with stage (f);

(i) filtering the extracted slurry obtained from stage (h) to again obtain a filter cake of wet defatted thyroglobulin; and (j) drying the defatted thyroglobulin for a sufficient time period at a temperature of 60°–70° C.

In conventional processes designed to meet USP XX specifications involving saline digestion of ground hog thyroid glands, subsequent treatment of the resultant aqueous saline solution comprises the steps of precipitating, denaturing, and defatting thyroglobulin. It has now been determined that the time periods involved with three of these steps, namely, precipitating, denaturing, and defatting, are important with respect to achieving the desired $T_4/T_3$ ratio of the final product to meet USP XXII specifications. The longer the time periods for performance of denaturing and defatting, generally the lower the $T_4/T_3$ ratio of the final product. Thus, by controlling the period of time spent during these individual steps in the thyroglobulin production process, one can attain a thyroglobulin product having a $T_4/T_3$ ratio consistently within the preferred range of about 2.6–3.4, and a preferred absolute amount of each active component.

An important aspect of this invention is the discovered correlation between the precipitation step and the denaturation and defatting steps. It has been found that the $T_4/T_3$ ratio increases as the duration of the precipitation step increases (primarily as a function of the duration of the acidic precipitation step preferred below (e.g., pH=4.4 at 46° C.). See FIG. 1. It has further been found that $T_4/T_3$ ratio is sensitive to duration of the denaturing step and defatting step(s), decreasing with both denaturing and defatting duration. Thus, for the invention, these steps can be consolidated to produce the final $T_4/T_3$ ratio of 2.6–3.4. The longer the precipitation step (and thus the higher the resultant intermediate $T_4/T_3$ ratio), the longer will be the denaturing and/or defatting steps (and thus the more the $T_4/T_3$ ratio after precipitation will be lowered) effective to produce a ratio of 2.6–3.4 and absolute proteolytic active ingredient concentrations.

The initial separation of thyroglobulin from the hog thyroid glands occurs during the digestion step. In this step, hog thyroid glands, preferably frozen, are ground and added to a saline digestion solution in order to extract thyroglobulin from the meat tissue. The resultant digestion mixture is maintained at a temperature of about 0°–5° C., while preferably being agitated for a sufficient period of time. To obtain a beneficial yield of thyroglobulin, a digestion time of about 16–24 hours is preferred.

Following digestion, waste meat tissue is separated from the mother liquor containing thyroglobulin extract by, for example, centrifugation or filtration. The separation step is preferably performed at or about the temperature of the digestion step. The filtrate is a stable solution and thus will not appreciably deteriorate over an extended period of time, e.g., up to 3–4 weeks when kept at about 0°–5° C.

After the separation step, the thyroglobulin extract is heated to a temperature of about 43° C.–49° C., and especially about 46° C. The pH of the liquor is adjusted by the addition of an acid solution such as a solution of acetic acid to induce precipitation and denaturation of crude thyroglobulin. The pH is adjusted to about 4.2–4.6, especially about 4.4. If pH is adjusted to a value above or below the preferred pH of about 4.4, a decrease in overall thyroglobulin yield may result. Following pH adjustment, the mother liquor is heated to a higher temperature of about 84° C.–86° C., especially about 86° C. for final denaturation.

During the precipitation phase, it has been found that the $T_4/T_3$ ratio increases with time. This increase in the ratio is apparently due to a decrease in $T_3$ concentration and an increase in $T_4$ concentration. For this reason, these precipitation steps of heating, adjusting pH, and again heating to 86° C. are preferably carried out within a short period of total time, e.g., about 0.4–0.6 hour, especially about 0.5 hour. If the thyroglobulin extract is, for example, held too long at the lower temperature plateau (e.g., 46° C.), too high an increase in the $T_4/T_3$ ratio and also a decrease in overall yield could result.

Following the heating to a higher temperature after the pH adjustment step, the mother liquor is held at this higher temperature to induce denaturing and precipitation of the substituents therein. While it is recognized that some denaturation occurs during precipitation, it is this hold period at a higher temperature which is referred to as the denaturing step of the invention. As mentioned earlier, the time period for the denaturing step has been found to be an important parameter with respect to the $T_4/T_3$ ratio. As the time period during which the mother liquor is held at the denaturing temperature increases, the $T_4/T_3$ ratio generally decreases. The decrease in the $T_4/T_3$ ratio is caused by a reduction in $T_4$ concentration and an increase in $T_3$ concentration. In accordance with the process according to the invention, the mother liquor is held at the denaturing temperature (i.e., preferably about 86° C.) for a time period of about 2.8–3.2, especially about 3 hours.

After the mother liquor or thyroglobulin extract is held at the preferred denaturing temperature for a sufficient period of time, the extract is cooled to a temperature of about 55°–65° C., especially about 60° C. Then, the extract is filtered to separate the crude precipitated thyroglobulin from the aqueous filtrate. For example, filtering can be initiated when the extract reaches a temperature of about 94° C.–82° C., especially about 60° C., during the cooling procedure.

The wet crude thyroglobulin collected as filter cake in the filtration following the denaturing step is further treated in a dewatering and defatting procedure. During this procedure, the wet crude thyroglobulin is mixed with alcohol or a mixture of alcohols to form a slurry, the alcohol functioning as a fat extraction solvent. A suitable alcohol is ethanol.

Once the crude wet thyroglobulin is suspended in the solvent to form a slurry, the slurry is then heated at a gentle reflux. Generally, during this extraction step, the slurry is heated to a temperature of about 74° C.–82° C., especially about 78° C.

As mentioned above, the time period for defatting is an important parameter with respect to the resultant $T_4/T_3$ ratio of the product. For this reason, the slurry is held at reflux during the defatting/dewatering step for a time period of about 1.4–1.6, especially about 1.5 hours. Following two such extraction procedures, the hot slurry is filtered and washed with solvent. The filtrate and any wash liquor are discarded or delivered to a solvent recovery system. The defatted thyroglobulin which is removed as the solid filter cake is then dried. The wet defatted thyroglobulin filter cake can, for example, be tray dried at a temperature of about 60°–70° C., for a time period sufficient to render the thyroglobulin product essentially free of solvent. The resultant dry defatted thyroglobulin powder can then be further worked up, e.g., by milling and screening, e.g., to a particle size of below about 40 mesh. The product thyroglobulin powder can be used, for example, in the manufacture of Proloid ® tablets. The product powder is a tan- or cream-colored, free-flowing powder having a slight characteristic odor.

In the discussion above, the invention has been described with respect to preferred aspects and embodiments. However, one of ordinary skill, in view of the guidance of this specification, can easily select other embodiments within the scope of the invention using no more than routine experimentation. For example, using a given time period for the denaturing step and a given time period for the extraction time, one can by routine experimentation parameterize the precipitation time so as to obtain the desired $T_4/T_3$ ratio. Similarly, details of any given step or combination of steps can be readily determined by routine parameter tests.

BRIEF DESCRIPTION OF THE DRAWINGS

Various other objects, features, and attendant advantages of the present invention will be more fully understood as the same becomes better understood when considered in conjunction with the accompanying drawing.

Figure 1:
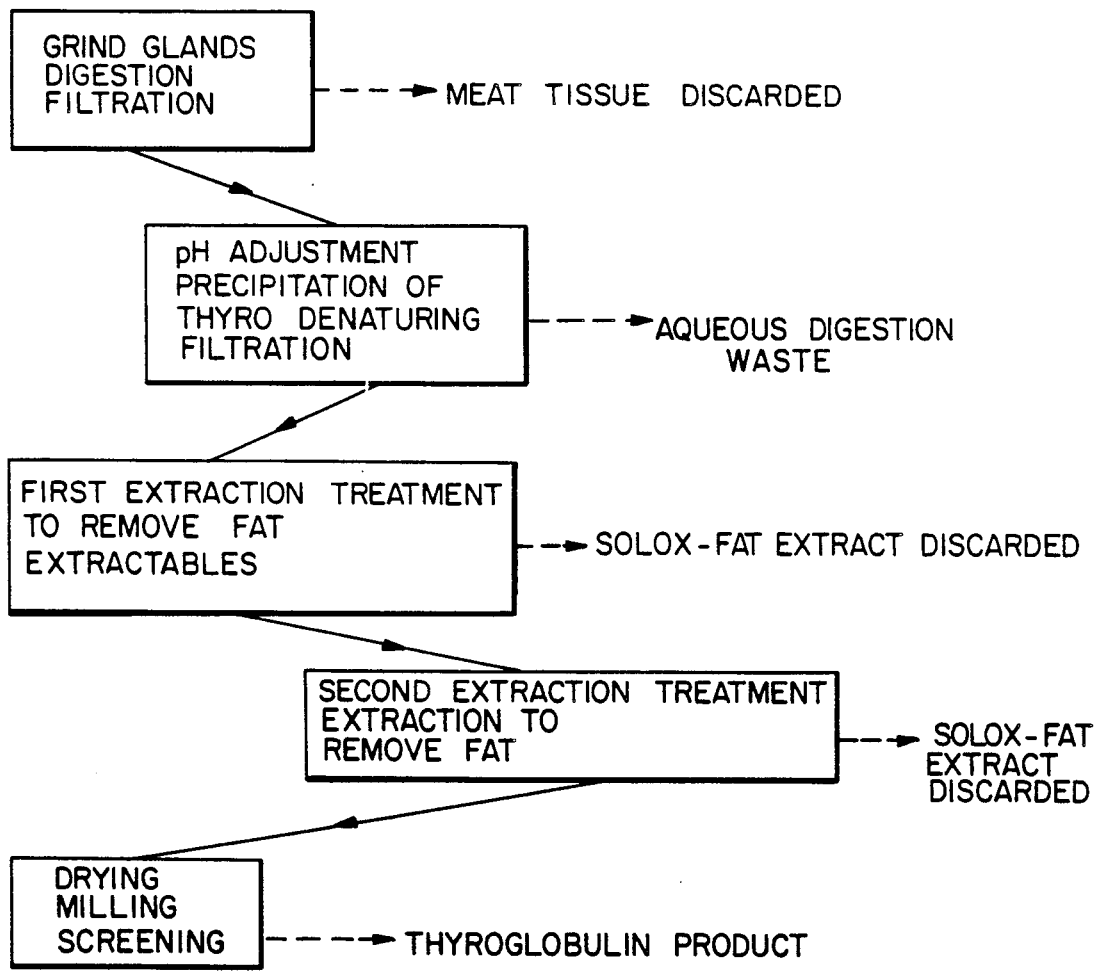
FIG. 1 illustrates a flowchart of the thyroglobulin process.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following example, all temperatures are set forth uncorrected in degrees Celsius; and, unless otherwise indicated, all parts and percentages are by weight.

The entire texts of all applications, patents and publications, cited above and below, are hereby incorporated by reference.

EXAMPLES

1A. Preparation of Stock Digest Solution

| Materials | |
|---|---|
| Water | 4.5 gal. |
| NaCl | 0.412 lbs. |
| Sodium salicylate | 0.03 kgs. |
| Celite "545" | 0.92 lbs. |
| Frozen ground hog thyroid glands | 15.0 lbs. (N-12584) |
| Water wash | 0.6 gal. |
| Celite "545" filter coating | 1.0 lb. |

Ground Hog Thyroid Glands

Frozen thyroid glands are slowly pressed through a Model K Fitzmill machine. The meat tissue is generally ground to pieces of about ½-inch in size. The ground glands are collected in a plastic bag placed on a tray at the hopper exit. These glands are immediately weighed and charged to a processing plant (15.0 lbs).

Digestion Procedure 4.5 gal of water are charged to the digestion tank. 0.412 lb. NaCl and 0.3 kg sodium salicylate are added and dissolved with agitation. The 15.0 lbs. of frozen ground hog thyroid glands are then added, and the funnel is rinsed with 0.6 gal of water. The mixture is continually stirred overnight while a temperature of 0°-5° C. is maintained.

The next day, 0.92 lbs. Celite "545" is slowly added to the digestion tank and mixed thoroughly for 1 hour. While the mixture is stirred, two 25 cm Buchner funnels and one 32 cm table top filter containing appropriately cut centrifuge cloth and backed up with Whatman No. 5 filter paper are precoated with Celite "545". These three funnels are then used to vacuum filter the digest.

Filtration of the digest mixture is begun after about 23.5 hours. The mixture is removed via a bottom outlet and introduced into a 4 liter beaker. The vacuum filtration proceeds very slowly, e.g., about 6 hours to completion. A total of about 4 gals of filtered saline solution is obtained and can be stored in a refrigerator at 0°-5° C.

1B. Preparation of Thyroglobulin

Materials

1. Stock solution of dilute acetic acid prepared by mixing 145 grams glacial acetic acid with 1250 grams of $H_2O$.
2. Stock solution (23.5 hours) of filtered digest solution stored at 0°-5° C. in refrigerator.

Isolation Method

A 200-ml aliquot of the 23.5 hour stock filtered digest solution is transferred to a 400-ml beaker. The solution is agitated with magnetic stirring and warmed to 46° C. The pH of the solution is adjusted to 4.4±0.1 by dropwise addition of stock dilute acetic acid solution. The amount of acid needed is usually 8.0 ml.

The thyro solution is heated to the desired denaturing temperature, i.e., about 86° C. These steps of heating, pH adjustment, and heating should be completed in about 0.5 hours. The solution is next transferred to the 250-ml three-necked flask previously placed in the silicon oil constant temperature bath, preheated to the desired temperature (standard setting at 86° C.).

The temperature is held at 86° C. until the time between ascending 82° C. and descending 82° C. reaches a total of 3 hours. The solution is then cooled to 60° C., at which time filtering is begun.

The funnel is equipped with 11.0 cm cut centrifuge cloth and backed up with Whatman No. 3 paper. The cake is washed with 200 ml of water. Filtration time is about 30 minutes. The filter cake is sucked dry for about 15 minutes. The water wet thyro is removed from the funnel via spatula and stored in 4 oz. amber bottles.

1C. Thyroglobulin Defatting

Materials

1. Virgin Denatured Alcohol
2. Crude water wet thyro samples

Defatting Procedure

The crude wet thyro is charged to a 250-ml flask (15-20 grams) equipped with reflux condenser. 167 ml of virgin denatured alcohol are added and gently refluxed with agitation on a magnetic stirrer hot plate. The slurry is held at reflux until the time between ascending 72° C. and descending 72° C. reaches 1.5 hours. The hot mixture is vacuum filtered using a 4.0 cm cloth-lined Buchner funnel backed up with a Whatman No. 4 filter paper. The filter cake is washed with 50 ml of hot alcohol and sucked dry for 5 minutes.

The defatted thyro is removed from the funnel and charged back to the 250-ml flask, where it is extracted again with 167 ml alcohol at reflux. The slurry is held at reflux until the time between ascending 72° C. and descending 72° C. reaches 1.5 hours. The filter cake is washed with 50 ml of hot alcohol and sucked dry for 5 minutes. The defatted thyro is collected by vacuum filtration.

The wet thyro is transferred to a tared pyrex dish and dried overnight at 60° C. in a hot air circulating oven.

Test Results

Several runs were made in general accordance with the above example of the thyroglobulin production process according to the invention. The results are set forth below in Table I.

TABLE I

| Run No. | $T_4$ | $T_3$ | $T_4/T_3$ | Denat. Extract (hrs/°C.) | Combined Solvent Time |
|---|---|---|---|---|---|
| 1 | 3.0 | 0.9 | 3.1 | 3/86 | 3 hrs. |
| 2 | 3.7 | 0.89 | 4.1 | 1.5/86 | 3 hrs. |
| 3 | 0.7 | 1.41 | 0.5 | 18/86 | 2 hrs. |

The preceding example can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of thyroglobulin having a thyroxine-to-triiodothyronine ratio ($T_4/T_3$ ratio) comprising saline digestion mammalian thyroid glands to release thyroglobulin, precipitation of thyroglobulin by pH adjustment, denaturation of thyroglobulin by heating, and defatting thyroglobulin by extraction with alcohol, the improvement comprising:
   correlating the precipitating, denaturing, and defatting steps whereby the duration of the precipitating step is selected to produce thyroglobulin having a first $T_4/T_3$ ratio substantially greater than 2.6 and the durations of the denaturing and defatting steps are selected in correlation with said precipitating step duration to lower said $T_4/T_3$ value greater than 2.6 to a final value in the range of 2.6–3.4 and absolute levels of not less than about 0.7 μg/mg liothyronine and not less than about 2.1 μg/mg levothyroxine.

2. A process according to claim 1, wherein said final $T_4/T_3$ ratio is about 3.0 and said glands are from hogs.

3. A process according to claim 1, wherein saline digestion is of hog thyroid glands and is performed at about 0°–5° C. for about 16–24 hours.

4. A process according to claim 1, wherein the denaturing step is performed at a temperature of about 86° C. for a time period of about 3 hours.

5. A process according to claim 1, wherein the defatting step comprises at least two separate extractions of thyroglobulin with alcohol under reflux wherein both extractions are performed at a temperature of at least about 78° C. and for a time period of at least about 1.5 hours.

6. A process according to claim 4, wherein the defatting step comprises at least two separate extractions of thyroglobulin with alcohol under reflux wherein both extractions are performed at a temperature of at least about 78° C. and for a time period of at least about 1.5 hours.

7. A process according to claim 1, wherein the step of precipitating thyroglobulin comprises (a) heating to about 46° C., (b) adjusting the pH to about 4.4, and (c) heating to about 86° C., and wherein steps (a)–(c) are performed within a time period of about 0.5 hour.

8. A process according to claim 1, wherein the step of precipitating thyroglobulin comprises adjusting the pH to about 4.4 by the addition of dilute acetic acid solution.

9. A process according to claim 1, wherein the saline digestion is of hog thyroid glands and comprises digesting ground hog thyroid glands in an aqueous solution containing NaCl and sodium salicylate.

10. A process according to claim 8, wherein following saline digestion, the aqueous solution containing thyroid glands is filtered to remove waste meat tissue, and the resultant thyroglobulin extract filtrate is denatured by heating.

11. A process according to claim 1, wherein after precipitation of thyroglobulin, the resultant mixture is subjected to filtration, and the resultant filtered cake of wet thyroglobulin is subjected to the defatting step.

12. A process for the production of thyroglobulin comprising:
   (a) digesting hog thyroid glands by adding ground hog thyroid glands to an aqueous saline solution of NaCl and sodium salicylate at a temperature of about 0°–5° C. and for a time period of about 16–24 hours;
   (b) following digestion, separating the resultant mixture into waste tissue and an aqueous solution of thyroglobulin extract;
   (c) heating the extract to about 46° C., adjusting the pH thereof to about 4.4, and then heating the extract to about 86° C., wherein the total time required for the performance of stage (c) is about 0.5 hour;
   (d) denaturing and precipitating the extract by holding the filtrate at a temperature of about 86° C. for a time period of about 3 hours;
   (e) cooling the extract to a temperature of about 60° C. and, while cooling, filtering the extract to obtain a filter cake of wet crude thyroglobulin;
   (f) forming a slurry of said wet crude thyroglobulin with alcohol and heating the resultant slurry to reflux, thereby defatting the wet thyroglobulin by extraction, wherein extraction is performed for a time period of about 1.5 hours;
   (g) filtering the slurry following extraction to again obtain a filter cake of once-extracted thyroglobulin;
   (h) forming a slurry by mixing once-extracted thyroglobulin with alcohol and again performing extraction in accordance with stage (f);
   (i) filtering the extracted slurry obtained from stage (h) to again obtain a filter cake of wet defatted thyroglobulin; and
   (j) drying said defatted thyroglobulin for a sufficient time period at a temperature of 60°–70° C.

13. A process for the production of thyroglobulin having a thyroxine-to-triiodothyronine ($T_4/T_3$) ratio about 2.6–3.4 from a mammalian thyroglobulin extract, comprising:

(a) precipitating said thyroglobulin extract by adjusting pH and by heating for a time sufficient to provide a $T_4/T_3$ ratio substantially greater than 2.6;

(b) determining by parametric experiments the time of subsequent denaturing and defatting treatments of the resultant thyroglobulin effective to denature and defat the thyroglobulin and to lower said $T_4/T_3$ ratio greater than 2.6 to a value in the range of 2.6–3.4 and absolute levels of not less than about 0.7 μg/mg liothyronine and not less than about 2.1 μg/mg levothyroxine;

(c) denaturing thyroglobulin by heating to a temperature higher than the temperature of precipitation and maintaining the higher temperature in accordance with the time determined in step (b); and (d) defatting thyroglobulin by extraction with alcohol under reflux in accordance with the time determined in step (b).

14. A process of claim 13, wherein the extract is from saline digestion of hog thyroid glands.

15. A process for the production of thyroglobulin from thyroglobulin extract produced from the saline digestion of hog thyroid glands, comprising:

(a) precipitating thyroglobulin by pH adjustment of said thyroglobulin extract;

(b) denaturing said thyroglobulin extract by heating; and (c) defatting thyroglobulin by extraction with alcohol;

wherein the durations of steps (b) and (c) are selected to adjust for an increase in $T_4/T_3$ ratio occurring during step (a) and wherein when the process is repeated at least 60% of the process runs yield defatted thyroglobulin product with a $T_4/T_3$ ratio of about 2.6–3.4 and absolute levels of not less than about 0.7 μg/mg liothyronine and not less than about 2.1 μg/mg levothyroxine.

16. A process for the production of thyroglobulin from thyroglobulin extract produced from the saline digestion of hot thyroid glands, comprising:

(a) precipitating thyroglobulin by pH adjustment of said thyroglobulin extract;

(b) denaturing said thyroglobulin extract and heating; and (c) defatting thyroglobulin by extraction with alcohol;

wherein the duration of steps (b) and (c) are sufficient to decrease the $T_4/T_3$ ratio of the thyroglobulin and wherein when the process is repeated at least 60% of the process runs yield a defatted thyroglobulin product with a $T_4/T_3$ ratio of about 2.6–3.4 and absolute levels of not less than about 0.7 μg/mg liothyronine and not less than about 2.1 μg/mg levothyroxine.

17. A process for the production of thyroglobulin having a thyroxine-to-triiodothyronine ($T_4/T_3$) ratio of about 2.6–3.4 from denatured mammalian thyroglobulin obtained having a $T_4/T_3$ ratio substantially greater than 2.6, comprising:

defatting thyroglobulin by extraction with alcohol for a time sufficient to achieve a $T_4/T_3$ ratio in the defatted thyroglobulin of about 2.6–3.4 and absolute levels of not less than about 0.7 μg/mg liothyronine and not less than about 2.1 μg/mg levothyroxine, said time having been determined by parametric experiments varying defatting time for a given $T_4/T_3$ ratio in said denatured mammalian thyroglobulin.

18. A process according to claim 12, wherein the product thyroglobulin has absolute values of not less than about 0.7 μg/mg liothyronine and not less than about 2.1 μg/mg levothyroxine.

* * * * *